US012806172B2

(12) United States Patent
El Azouzi

(10) Patent No.: US 12,806,172 B2
(45) Date of Patent: Nov. 24, 2026

(54) CARDIOVASCULAR DISEASE MEDICATION ADMINISTRATION METHODS

(71) Applicant: AORTO MEDICAL LLC, Tangier (MA)

(72) Inventor: Youssef El Azouzi, Tangier (MA)

(73) Assignee: AORTO MEDICAL LLC, Tangier (MA)

( * ) Notice: Subject to any disclaimer, the term of this patent is extended or adjusted under 35 U.S.C. 154(b) by 593 days.

(21) Appl. No.: 18/275,659

(22) PCT Filed: Feb. 4, 2022

(86) PCT No.: PCT/IB2022/051006
§ 371 (c)(1),
(2) Date: Aug. 3, 2023

(87) PCT Pub. No.: WO2022/168004
PCT Pub. Date: Aug. 11, 2022

(65) Prior Publication Data

US 2024/0123204 A1 Apr. 18, 2024

Related U.S. Application Data

(60) Provisional application No. 63/156,356, filed on Mar. 4, 2021, provisional application No. 63/148,385, filed
(Continued)

(51) Int. Cl.
*A61K 31/404* (2006.01)
*A61F 2/06* (2013.01)
(Continued)

(52) U.S. Cl.
CPC .............. *A61K 31/404* (2013.01); *A61F 2/07* (2013.01); *A61K 31/138* (2013.01);
(Continued)

(58) Field of Classification Search
CPC .. A61K 31/404; A61K 31/138; A61K 31/216; A61K 31/401; A61K 31/41;
(Continued)

(56) References Cited

U.S. PATENT DOCUMENTS

| | | | | |
|---|---|---|---|---|
| 7,780,628 B1 * | 8/2010 | Keren | A61M 60/237 | 604/101.03 |
| 2005/0004663 A1 * | 1/2005 | Llanos | A61B 17/11 | 623/1.46 |
| 2012/0239131 A1 * | 9/2012 | Sulaimon | A61L 31/16 | 623/1.42 |

FOREIGN PATENT DOCUMENTS

WO WO2020168216 A1 8/2020

OTHER PUBLICATIONS

Clark; Change in renal function associated with drug treatment in heart failure: national guidance; Heart (British Cardiac Society), Jun. 1, 2019, pp. 904-910, XP055911859, DOI: 10.1136heartjnl-2018-314158; from URL:https://heart.bmj.com/content/heartini/105/12/904.1ullpdi (Year: 2019).*
(Continued)

*Primary Examiner* — David N Brandt
(74) *Attorney, Agent, or Firm* — K&L Gates LLP

(57) ABSTRACT

Medication administration methods are provided for treating cardiovascular disease. A method may include administering a baseline dosage of the medication to a patient. A flow diverting apparatus may be implanted into a vessel of the patient such that blood pressure to the patient's kidneys is increased. The flow diverting apparatus is structured to partially occlude blood flow through the vessel when implanted thereby increasing upstream blood pressure. Subsequent to implanting the flow diverting apparatus, the medication dosage may be increased above, or decreased below, the baseline dosage. The dosage may be increased if the medication is a beta-blocker, an angiotensin-receptor
(Continued)

Mocker, an angiotensin receptor enzyme inhibitor, a chymase inhibitor, a combination of an angiotensin receptor enzyme inhibitor and an angiotensin-receptor blocker, or a combination of an angiotensin receptor blocker and a neprilysin-inhibitor. The dosage may be decreased if the medication is a diuretic.

16 Claims, 5 Drawing Sheets

Related U.S. Application Data on Feb. 11, 2021, provisional application No. 63/146,150, filed on Feb. 5, 2021.

(51) Int. Cl.

| | |
|---|---|
| ***A61F 2/07*** | (2013.01) |
| ***A61F 2/82*** | (2013.01) |
| ***A61K 31/138*** | (2006.01) |
| ***A61K 31/216*** | (2006.01) |
| ***A61K 31/401*** | (2006.01) |
| ***A61K 31/4178*** | (2006.01) |
| ***A61K 31/4184*** | (2006.01) |
| ***A61K 31/551*** | (2006.01) |
| ***A61K 38/06*** | (2006.01) |
| ***A61K 45/06*** | (2006.01) |
| ***A61P 9/04*** | (2006.01) |

(52) U.S. Cl.

CPC .......... *A61K 31/216* (2013.01); *A61K 31/401* (2013.01); *A61K 31/4178* (2013.01); *A61K 31/4184* (2013.01); *A61K 31/551* (2013.01); *A61K 38/06* (2013.01); *A61K 45/06* (2013.01); *A61P 9/04* (2018.01); *A61F 2002/068* (2013.01); *A61F 2/82* (2013.01); *A61F 2230/001* (2013.01)

(58) Field of Classification Search

CPC ............ A61K 31/4178; A61K 31/4184; A61K 31/551; A61K 38/06; A61K 45/06; A61F 2/07; A61F 2/82; A61F 2002/068; A61F 2230/001; A61P 9/04

See application file for complete search history.

(56) References Cited

OTHER PUBLICATIONS

Sica; Combination Angiotensin-Converting Enzyme Inhibitor and Angiotensin Receptor Blocker Therapy_ Its Role in Clinical Practice—PMC; from pmc.ncbi.nlm.nih.gov/articles/PMC8099326/ (Year: 2007).*

Drugs.com; Valsartan Dosage Guide with Precautions—Drugs.com; from web.archive.org/web/20190403172757/https://www.drugs.com/dosage/valsartan.html (Year: 2019).*

Drugs.com; Enalapril Dosage Guide with Precautions—Drugs.com; from web.archive.org/web/20190921113448/https://www.drugs.com/dosage/enalapril.html (Year: 2019).*

Drugs.com; List of Cardioselective beta blockers—Drugs.com; from web.archive.org/web/20190418043031/https://www.drugs.com/drug-class/cardioselective-beta-blockers.html (Year: 2019).*

Drugs.com; Metoprolol Dosage Guide with Precautions—Drugs.com; from web.archive.org/web/20190427105609/https://www.drugs.com/dosage/metoprolol.html (Year: 2019).*

International Search Report for related International Application No. PCT/IB2022/051006; action dated Feb. 5, 2021; (3 pages).

Clark Andrew L et al: "Change in renal function associated with drug treatment in heart failure: national guidance", Heart (British Cardiac Society), Jun. 1, 2019 (Jun. 1, 2019), pp. 904-910, XP055911859, England URL: https://heart.bmj.com/content/heartjnl/105/12/904.full.pdf.

International Preliminary Report on Patentability for related International Application No. PCT/IB2022/051006; action dated Aug. 17, 2023; (8 pages).

* cited by examiner

CARDIOVASCULAR DISEASE MEDICATION ADMINISTRATION METHODS

PRIORITY CLAIM

The present application is a National Stage of International Application No. PCT/IB2022/051006, filed on Feb. 4, 2022, which claims priority to and the benefit of U.S. Provisional Application Nos. 63/146,150, filed Feb. 5, 2021; 63/148,385, filed Feb. 11, 2021; and 63/156,356, filed Mar. 4, 2021, the entirety of each of which is herein incorporated by reference.

TECHNICAL FIELD

The present application relates generally to cardiovascular disease treatment. More specifically, the present application provides methods of increasing or decreasing the medication dosages prescribed to cardiovascular disease patients through the use of an implanted flow diverting apparatus.

BACKGROUND

In various treatment applications, including but not limited to congestive heart failure, myocardial infarction and post-surgical recovery, medications including angiotensin receptor enzyme (ACE) inhibitors, angiotensin-receptor blockers, neprilysin inhibitors and chymase inhibitors can be used to mitigate and prevent further progression of myocardial disease processes. They have played a vital and pivotal role in enhancing quality of life and reducing mortality in affected patients because they all slow down fibrosis-related cardiac remodelling following myocardial ischemia or other forms of cardiac injury that is mediated by neurohormones such as angiotensin H. Thus, as pathological cardiac remodelling involves the depredation of functional myocardium into fibrotic scar tissue, these medications have formed the backbone of management for these patients to preserve functionality of their hearts as well as the kidneys by preventing fibrotic transformation of healthy cardiac parenchyma. They are also important in reducing the systemic resistance of blood vessels throughout the body via vasodilation and are therefore responsible for reducing blood pressure. This has the effect of reducing afterload on the left ventricle, which further enhances delivery of oxygenated blood to the rest of the body due to stronger contractility of the cardiac muscle, thus increasing stroke volume. This relationship can be further assessed in the well-known frank-starling curve.

In some instances, a patient may be prescribed a single ACE inhibitor, a single angiotensin-receptor blocker, a single neprilysin inhibitor, or a single chymase-inhibitor individually. In other instances, a patient may be prescribed a combination of: (i) an ACE inhibitor and an angiotensin-receptor blocker or (ii) an angiotensin-receptor blocker and a neprilysin inhibitor. Such other instances may be referred to as a combination therapy. Combination therapy can be administered in certain patients that have already been administered an individual medication (e.g., an ACE inhibitor or an angriotensin-receptor blocker) in order to yield better clinical outcome in patients suffering from cardiovascular diseases such as congestive heart failure. Stated differently, in one example, a patient may be administered with an ACE inhibitor first and then may subsequently be administered with an angiotensin-receptor blocker in addition to the ACE inhibitor if the ACE inhibitor alone is not yielding a desired clinical outcome. In another example, a patient may be administered with an angiotensin-receptor blocker first and then may subsequently be administered neprilysin inhibitor in addition to the angiotensin-receptor blocker if the angiotensin-receptor blocker alone is not yielding a desired clinical outcome.

Although the aforementioned medications are important in short and long-term hemodynamic stabilization of patients suffering from cardiovascular diseases, they cannot be used at dosages higher than those normally administered in clinical practice because they may induce certain side effects. Side effects may prevent patients from tolerating certain dosages of ACE inhibitors, angiotensin receptor blockers and/or neprilysin inhibitors for an extended period of time despite the fact that these medications are life-saving, Beyond the maximum-tolerated dosage, the emergence of these side effects include decreased upper body blood pressure (which can cause dizziness and confusion due to lower blood pressure to the brain), elevated levels of serum creatinine (which is a sign of kidney injury due to reduced kidney blood pressure as well as reduced glomerular filtration rate) and elevated serum potassium levels (which can cause abnormal heart rhythms) among other side effects.

In addition, despite the beneficial physiological effects of combination therapy on the heart's overall function, a significant number of patients are unable to tolerate such a treatment protocol due to systemic side effects such as hypotension as well as side effects specific to the kidneys. One or multiple side effects force some patients to discontinue such a combination therapy protocol and may prevent other patients from starting such a combination therapy in the first place. Additionally, patients who suffer from concomitant conditions such as chronic kidney disease are less likely to be able to tolerate single medication use or combination use due to drug-induced deterioration of kidney function. Accordingly, a need exists for a method that counteracts or offsets the negative effects of ACE inhibitors, angiotensin receptor blockers and neprilysin inhibitors in a relatively safe manner in order to help permit patients to yield maximum benefit from these drugs without being compelled to reduce their dosage or completely abandon their life-sustaining use.

SUMMARY

The present application provides new and innovative titration methods for increasing or decreasing the dosage of one or more medications prescribed to a patient with cardiovascular disease through the use of an implanted flow diverting apparatus. In some aspects, a dosage (e.g., mg/day) of a beta-blocker, an angiotensin-receptor blocker, an angiotensin receptor enzyme (ACE) inhibitor, a chymase inhibitor, or a combination therapy of drugs for cardiovascular disease treatment may be increased one or more times following the implantation of a flow diverting apparatus within a patient. In various examples, an increased dosage may be maintained for a monitoring period (e.g., one or two weeks) before increasing the dosage again. In other aspects, a dosage of a diuretic may be decreased following the implantation of a flow diverting apparatus within a patient. The implanted flow diverting apparatus can help reduce or eliminate the medication side effects that the patient experiences when a dosage of a beta-blocker, an angiotensin-receptor blocker, an angiotensin receptor enzyme (ACE) inhibitor, a chymase inhibitor, or a combination therapy of these drugs is increased above a baseline dosage, which thereby enables administering a higher dosage to the patient. The implanted flow diverting apparatus can further help reduce the medication side effects that a patient experiences from being administered diuretics by enabling a decrease in the diuretics dosage below a baseline dosage. In this way, the provided titration methods involving the implantation of a flow diverting apparatus help increase cardiovascular disease treatment effectiveness with these medications.

In light of the technical features set forth herein, and without limitation, in a first aspect of the disclosure in the present application, which may be combined with any other aspect unless specified otherwise, a method for administering at least one medication includes administering a respective dosage of each of the at least one medication to a patient at a respective baseline dosage. A flow diverting apparatus is then implanted in the patient receiving the respective baseline dosage of each of the at least one medication, relative to a vessel of the patient, such that blood pressure to the kidneys and/or brain of the patient is increased. The flow diverting apparatus is configured to partially occlude blood flow through the vessel when implanted to thereby increase blood pressure upstream the implanted flow diverting apparatus. Subsequent to implanting the flow diverting apparatus, the respective dosage of one or more of the at least one medication is increased above the respective baseline dosage. The at least one medication is: (i) an angiotensin-receptor blocker. (ii) an angiotensin receptor enzyme (ACE) inhibitor, (iii) a chymase inhibitor, (iv) an angiotensin receptor enzyme (ACE) inhibitor and an angiotensin-receptor blocker, (v) an angiotensin receptor blocker and a neprilysin-inhibitor, or (vi) a beta-blocker and an angiotensin receptor enzyme (ACE) inhibitor, an angiotensin-receptor blocker, or a neprilysin inhibitor.

In a second aspect of the disclosure in the present application, which may be combined with any other aspect (e.g., the 1$^{st}$ aspect) unless specified otherwise, the flow diverting apparatus includes an inflatable member, a stent, or a stent-graft.

In a third aspect of the disclosure in the present application, which may be combined with any other aspect (e.g., the 1$^{st}$ or 2$^{nd}$ aspect) unless specified otherwise, the wherein the vessel is the infrarenal aorta or a vessel downstream the infrarenal aorta.

In a fourth aspect of the disclosure in the present application, which may be combined with any other aspect (e.g., the 1$^{st}$ through the 3$^{rd}$ aspects) unless specified otherwise, prior to implanting the flow diverting apparatus into the patient, a respective dosage of the at least one medication above the respective baseline dosage causes the patient to experience negative side effects of the at least one medication.

In a fifth aspect of the disclosure in the present application, which may be combined with any other aspect (e.g., the 1$^{st}$ through the 4$^{th}$ aspects) unless specified otherwise, the respective dosage of the one or more of the at least one medication is increased one or more times until a hemodynamic status of the patient is stable.

In a sixth aspect of the disclosure in the present application, which may be combined with any other aspect (e.g., the 1$^{st}$ through the 5$^{th}$ aspects) unless specified otherwise, the at least one medication is a first medication, the method further comprising administering a dosage of a second medication to the patient subsequent to implanting the flow diverting apparatus.

In a seventh aspect of the disclosure in the present application, which may be combined with any other aspect (e.g., the 6$^{th}$ aspect) unless specified otherwise, the second medication is an angiotensin receptor enzyme (ACE) inhibitor, an angiotensin receptor blocker, or a neprilysin-inhibitor.

In an eighth aspect of the disclosure in the present application, which may be combined with any other aspect (e.g., the 1$^{st}$ through the 7$^{th}$ aspects) unless specified otherwise, the method further includes increasing the respective increased dosage of the one or more of the at least one medication after a period of maintaining the respective increased dosage.

In a ninth aspect of the disclosure in the present application, which may be combined with any other aspect (e.g., the 8$^{th}$ aspect) unless specified otherwise, the period of maintaining the respective increased dosage is greater than or equal to one week and less than or equal to two weeks.

In a tenth aspect of the disclosure in the present application, which may be combined with any other aspect (e.g., the 1$^{st}$ through the 9$^{th}$ aspects) unless specified otherwise, the at least one medication is one of the angiotensin-receptor blockers in the group consisting of valsartan, losartan, candesartan, eprosartan, telmisartan, and irbesartan.

In an eleventh aspect of the disclosure in the present application, which may be combined with any other aspect (e.g., the 10$^{th}$ aspect) unless specified otherwise, if the at least one medication is valsartan, the respective dosage of valsartan is increased to a dosage within a range of greater than or equal to 40 and less than or equal to 320 mg/day; if the at least one medication is losartan, the respective dosage of losartan is increased to a dosage within a range of greater than or equal to 25 and less than or equal to 150 mg/day; if the at least one medication is candesartan, the respective dosage of candesartan is increased to a dosage within a range of greater than or equal to 8 and less than or equal to 32 mg/day; if the at least one medication is eprosartan, the respective dosage of eprosartan is increased to a dosage is within a range of greater than or equal to 500 and less than or equal to 800 mg/day; if the at least one medication is telmisartan, the respective dosage of telmisartan is increased to a dosage within a range of greater than or equal to 40 and less than or equal to 80 mg/day; and if the at least one medication is irbesartan, the respective dosage of irbesartan is increased to a dosage within a range of greater than or equal to 150 and less than or equal to 300 mg/day.

In a twelfth aspect of the disclosure in the present application, which may be combined with any other aspect (e.g., the 1$^{th}$ through the 9$^{th}$ aspects) unless specified otherwise, the at least one medication is one of the angiotensin receptor enzyme (ACE) inhibitors in the group consisting of enalapril, lisinopril, trandolapril, ramipril, captopril, quinapril, and cilazapril.

In a thirteenth aspect of the disclosure in the present application, which may be combined with any other aspect (e.g., the 12$^{th}$ aspect) unless specified otherwise, if the at least one medication is enalapril, the respective dosage of enalapril is increased to a dosage within a range of greater than or equal to 5 and less than or equal to 40 mg/day; if the at least one medication is lisinopril, the respective dosage of lisinopril is increased to a dosage within a range of greater than or equal to 5 and less than or equal to 40 crag/day; if the at least one medication is trandolapril, the respective dosage of trandolapril is increased to a dosage within a range of greater than or equal to 2 and less than or equal to 4 mg/day; if the at least one medication is ramipril, the respective dosage of ramipril is increased to a dosage within a range of greater than or equal to 2.5 and less than or equal to 10 cog/day; if the at least one medication is captopril, the respective dosage of captopril is increased to a dosage within a range of greater than or equal to 37.5 and less than or equal to 450 mg/day, if the at least one medication is quinapril, the respective dosage of quinapril is increased to a dosage within a range of greater than or equal to 10 and less than or equal to 40 mg/day; and if the at least one medication is cilazapril, the respective dosage of cilazapril is increased to a dosage within a range of greater than or equal to 1 and less than or equal to 5 mg/day.

In a fourteenth aspect of the disclosure in the present application, which may be combined with any other aspect (e.g., the $1^{st}$ through the $9^{th}$ aspects) unless specified otherwise, the at least one medication is an angiotensin receptor blocker and a neprilysin-inhibitor, and wherein the neprilysin-inhibitor is saccubitril.

In a fifteenth aspect of the disclosure in the present application, which may be combined with any other aspect (e.g., the $1^{th}$ through the $9^{th}$ aspects) unless specified otherwise, the at least one medication is (1) a beta-blocker and (2) an ACE-inhibitor, an angiotensin-receptor blocker, or a neprilysin inhibitor, and wherein the beta-blocker is one of the medications in the group consisting of bisoprolol, carvedilol, and metoprolol.

In a sixteenth aspect of the disclosure in the present application, which may be combined with any other aspect (e.g., the $15^{th}$ aspect) unless specified otherwise, if the beta-blocker is bisoprolol, the respective dosage of bisoprolol is increased to a dosage within a range of greater than or equal to 2.5 and less than or equal to 20 mg per day until the patient's hemodynamic status is stable; if the beta-blocker is carvedilol, the respective dosage of carvedilol is increased to a dosage within a range of greater than or equal to 6.25 and less than or equal to 100 mg per day until the patient's hemodynamic status is stable; and if the beta-blocker is metoprolol, the respective dosage of metoprolol is increased to a dosage within a range of greater than or equal to 25 and less than or equal to 200 mg per day until the patient's hemodynamic status is stable.

In a seventeenth aspect of the disclosure in the present application, which may be combined with any other aspect (e.g., the $2^{nd}$ and $3^{rd}$ aspects) unless specified otherwise, a method for administering a medication includes administering a dosage of a medication to a patient at a baseline dosage. A flow diverting apparatus is then implanted in the patient receiving the baseline dosage of the medication, relative to a vessel of the patient, such that blood pressure to the kidneys and/or brain of the patient is increased. The flow diverting apparatus is configured to partially occlude blood flow through the vessel when implanted to thereby increase blood pressure upstream the implanted flow diverting apparatus. Subsequent to implanting the flow diverting apparatus, the dosage of the medication is decreased below the baseline dosage. The medication is a diuretic.

In an eighteenth aspect of the disclosure in the present application, which may be combined with any other aspect (e.g., the $17^{th}$ aspect) unless specified otherwise, the flow diverting apparatus includes an inflatable member, a stent, or a stent-craft.

In a nineteenth aspect of the disclosure in the present application, which may be combined with any other aspect (e.g., $17^{th}$ or $18^{th}$ aspect) unless specified otherwise, the diuretic is one of the medications in the group consisting of furosemide, torsemide, bumetanide, metolazone, chlorothiazide, hydrochlorothiazide, indapamide, chlorothalidone, spironolactone, and eplerenone.

In a twentieth aspect of the disclosure in the present application, which may be combined with any other aspect (e.g., the $19^{th}$ aspect) unless specified otherwise, if the diuretic is furosemide, the respective dosage of furosemide is decreased to a dosage within a range of greater than or equal to 20 and less than or equal to 600 mg/day; if the diuretic is torsemide, the respective dosage of torsemide is decreased to a dosage within a range of greater than or equal to 20 and less than or equal to 200 mg/day; if the diuretic is bumetanide, the respective dosage of bumetanide is decreased to a dosage within a range of greater than or equal to 0.5 and less than or equal to 10 mg/day; if the diuretic is metolazone, the respective dosage of metolazone is decreased to a dosage within a range of greater than or equal to 2.5 and less than or equal to 300 mg/day; if the diuretic is chlorothiazide, the respective dosage of chlorothiazide is decreased to a dosage within a range of greater than or equal to 50 and less than or equal to 1000 mg/day; if the diuretic is hydrochlorothiazide, the respective dosage of hydrocholorthiazide is decreased to a dosage within a range of greater than or equal to 12.5 and less than or equal to 200 mg/day; if the diuretic is indapamide, the respective dosage of indapamide is decreased to a dosage within a range of greater than or equal to 1.25 and less than or equal to 3.75 mg/day; if the diuretic is chlorothalidone, the respective dosage of cholorothalidone is decreased to a dosage within a range of greater than or equal to 50 and less than or equal to 150 mg/day; if the diuretic is spironolactone, the respective dosage of spriolactone is decreased to a dosage within a range of greater than or equal to 25 and less than or equal to 200 mg/day; and if the diuretic is eplerenone, the respective dosage of eplerenone is decreased to a dosage within a range of greater than or equal to 25 and less than or equal to 50 mg/day.

In a twenty-first aspect of the disclosure in the present application, which may be combined with any other aspect (e.g., the $2^{nd}$ through the $16^{th}$ aspects) unless specified otherwise, at least one medication for use in a method of treating cardiovascular disease is provided. The at least one medication includes: (i) an angiotensin-receptor blocker, (ii) an angiotensin receptor enzyme (ACE) inhibitor, (iii) a chymase inhibitor, (iv) an angiotensin receptor enzyme (ACE) inhibitor and an angiotensin-receptor blocker, (v) an angiotensin receptor blocker and a neprilysin-inhibitor, or (vi) a beta-blocker and an angiotensin receptor enzyme (ACE) inhibitor, an angiotensin-receptor blocker, or a neprilysin inhibitor. The method includes administering a respective dosage of said at least one medication to a patient at a respective baseline dosage; and increasing the respective dosage of one or more of said at least one medication above the baseline dosage in conjunction with an implanted flow diverting apparatus.

In a twenty-second aspect of the disclosure in the present application, which may be combined with any other aspect (e.g., the $17^{th}$ through the $20^{th}$ aspects) unless specified otherwise, a medication for use in a method of treating cardiovascular disease is provided. The medication includes a diuretic. The method includes administering a dosage of said medication to a patient at a baseline dosage; and decreasing the dosage of said medication below the baseline dosage in conjunction with an implanted flow diverting apparatus.

In a twenty-third aspect of the disclosure in the present application, which may be combined with any other aspect (e.g., the $2^{nd}$ through the $20^{th}$ aspects) unless specified otherwise, at least one medication for use in a method of treating cardiovascular disease is provided. The at least one medication includes: (i) an angiotensin-receptor blocker, (ii) an angiotensin receptor enzyme (ACE) inhibitor, (iii) a chymase inhibitor, (iv) an angiotensin receptor enzyme (ACE) inhibitor and an angiotensin-receptor blocker, (v) an angiotensin receptor blocker and a neprilysin-inhibitor, (vi) a beta-blocker and an angiotensin receptor enzyme (ACE) inhibitor, an angiotensin-receptor blocker, or a neprilysin inhibitor, or (vii) a diuretic. The method includes administering a respective dosage of said at least one medication to a patient at a respective baseline dosage. If said at least one medication comprises (i) an angiotensin-receptor blocker, (ii) an angiotensin receptor enzyme (ACE) inhibitor, (iii) a chymase inhibitor, v) an angiotensin receptor enzyme (ACE) inhibitor and an angiotensin-receptor blocker, (v) an angiotensin receptor blocker and a neprilysin-inhibitor, or (vi) a beta-blocker and an angiotensin receptor enzyme (ACE) inhibitor, an angiotensin-receptor blocker, or a neprilysin inhibitor, then the method includes increasing the respective dosage of one or more of said at least one medication above the respective baseline dosage in conjunction an implanted flow diverting apparatus. If said at least one medication comprises a diuretic, then the method includes decreasing the respective dosage of said at least one medication below the baseline dosage in conjunction with an implanted flow diverting apparatus.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

Figure 1:
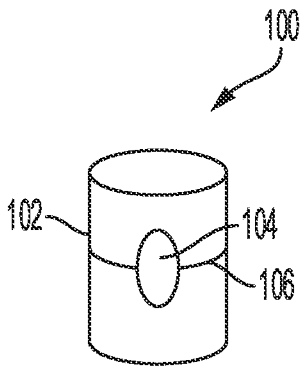
FIG. 1 illustrates a flow diverting apparatus having an inflatable balloon, according to an aspect of the present disclosure.

The present application provides new and innovative titration methods for increasing or decreasing the dosage of one or more medications prescribed to a patient with cardiovascular disease through integrating a therapeutic use of a flow diverting apparatus with the therapeutic administration of such medication(s). In various aspects, the one or more medications may be a beta-blocker, an angiotensin receptor blocker, an angiotensin receptor enzyme (ACE) inhibitor, and; or a neprilysin inhibitor, or one or more diuretics. A flow diverting apparatus may be implanted in a vessel of the patient such that blood pressure to the patient's kidneys and/or brain is increased. For instance, the flow diverting apparatus may be structured to at least partially occlude blood flow through the vessel, thereby increasing blood pressure proximal to (e.g., upstream) the implanted flow diverting apparatus, and the implanted flow diverting apparatus may be positioned such that the increased blood pressure is directed to the patient's kidneys and/or brain. In various examples, the flow diverting apparatus may be located in the vicinity of the patient's infrarenal aorta or in a more distal (e.g., downstream) blood vessel to the infrarenal aorta. For example, such a downstream blood vessel may be the right common iliac artery or superficial femoral artery and/or any other suitable blood vessel downstream the infrarenal aorta. As used herein, the terms "proximal to" or "upstream" indicate being closer to the patient's heart relative to the object being referenced, whereas the terms "distal to" or "downstream" indicate being further from the patient's heart relative to the object being referenced.

In at least some aspects, the patient may be undergoing a treatment plan of the one or more medications at a baseline dosage prior to implanting the flow diverting apparatus in the patient's vessel. For example, when the flow diverting apparatus is implanted, the patient may already be undergoing a treatment plan of: (i) an ACE-inhibitor, (ii) an angiotensin-receptor Mocker, (iii) a combination therapy of an ACE-inhibitor and an angiotensin-receptor blocker, (iv) a combination therapy of an angiotensin-receptor blocker and a neprilysin inhibitor, or (v) a combination therapy of a beta-blocker and an ACE-inhibitor, an angiotensin-receptor blocker, or a neprilysin inhibitor. The treatment plan may also include one or more diuretics. Implanting the flow diverting apparatus thereafter enables increasing or decreasing the dosage of the one or more medications above or below the baseline dosage, which the patient can otherwise not tolerate without the implanted flow diverting apparatus, to improve the patient's cardiovascular disease treatment. For instance, the dosage of an ACE-inhibitor, an angiotensin-receptor blocker, a neprilysin inhibitor, or a beta-blocker may be increased, whereas the dosage of a diuretic may be decreased.

More specifically, without the implanted flow diverting apparatus increasing blood pressure to the patient's kidneys and/or brain, a dosage of an ACE-inhibitor, angiotensin-receptor blocker, neprilysin inhibitor, and/or beta-blocker above the baseline dosage causes the patient to experience intolerable negative side effects of the ACE-inhibitor, angiotensin-receptor blocker, neprilysin inhibitor, and/or beta-blocker. The implanted flow diverting apparatus helps reduce or eliminate the negative side effects when such medication dosage is increased above the baseline dosage thereby enabling the patient to receive a higher medication dosage.

For instance, implanting the flow diverting apparatus such that it increases blood pressure to the kidneys enables restoration of more elevated kidney blood perfusion pressure due to the buildup of blood flow proximal to the implanted flow diverting apparatus, thus leading to increased intraglomerular pressure and hence a higher glomerular filtration rate, urine output and ultimately a reduction in severity of fluid retention-related symptoms commonly seen in heart failure patients. Normalization of kidney biomarker levels such as that of creatinine and potassium in the blood would therefore result due to a reversal of the kidney hypoperfusion state that was initially caused by single or combination therapy consisting of an ACE-inhibitor and/or angiotensin-receptor blocker, an angiotensin-receptor blocker and neprilysin inhibitor or a beta-blocker and any of the aforementioned medications. Furthermore, creating a build-up of blood pressure proximal to, or upstream, the flow diverter apparatus can also increase blood pressure to the brain and therefore reduce symptoms of upper body hypotension such as dizziness and confusion. Accordingly, the implanted flow diverting apparatus helps reduce or eliminate at least some side effects experienced by patients administered with an ACE-inhibitor and/or angiotensin-receptor blocker, an angiotensin-receptor blocker and neprilysin inhibitor, or a beta-blocker and any of the aforementioned medications thereby enabling such patients to be administered with a higher dosage of such medications.

Additionally, the restoration of more elevated kidney blood perfusion pressure due to the proximal buildup of blood flow through the use of a flow diverter apparatus helps increase urine output. This increased urine output helps enable doses of diuretics e.g., furosemide) to be decreased, or down-titrated, since a high dosage of diuretic(s) would no longer be necessary to achieve optimal diuresis. This has the added benefit of reducing potential side-effects related to the use of diuretic medications as a whole since a lower dose of the diuretic(s) is needed.

The flow diverting apparatus used in the provided methods may have any suitable structure such that it partially occludes flow through a vessel when implanted internal to or external to the vessel. For instance, the flow diverting apparatus may be structured such that, once implanted, it reduces the size of the vessel luminal area intravascularly or extravascularly in order to partially occlude flow through the vessel. If the flow diverting apparatus is implanted intravascularly, or internal to the vessel, the flow diverting apparatus may be structured such that blood must flow in a particular direction (e.g., to the renal artery branches) or through a smaller area through the flow diverting apparatus than the vessel. Stated differently, the flow diverting apparatus may have an inlet with a diameter substantially matching the vessel's diameter (e.g., the flow diverting apparatus' outer surface at the inlet is contacting the vessel wall) and may then narrow such that a portion of the flow diverting apparatus has a smaller diameter than the inlet diameter. If the flow diverting apparatus is implanted extravascularly, or external to the vessel, the flow diverting apparatus narrows a portion of the vessel itself such that a diameter of the vessel where the flow diverting apparatus is implanted is smaller than a diameter of the vessel upstream the implanted flow diverting apparatus. In one example, a segment of an extravascular flow diverting apparatus can be implanted within the patient's skin subcutaneously.

In various aspects, the flow diverting apparatus may be bare-metal stent based, stent-graft based, balloon and/or cuff based, coil-based, band-based, or any suitable combination thereof, to achieve the desired partial flow occlusion through a vessel.

Figure 2:
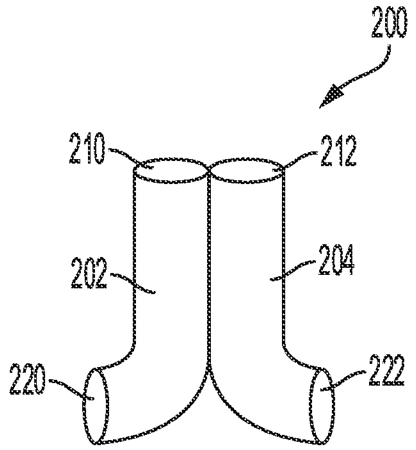
FIG. 2 illustrates a flow diverting apparatus based on one or more sets of interconnecting tubular structures, according to an aspect of the present disclosure.

FIG. 1 illustrates an example flow diverting apparatus 100 for an intravascular approach that includes a balloon 104 which can be inflated or deflated with any form of liquid or gas in order to obstruct the desired vessel lumen to the desired level in order for proximal blood pressure buildup to take place. The balloon 104 may be anchored or tethered to a frame 102 of the flow diverting apparatus 100 by attachments 106. In another example, FIG. 2 illustrates a flow diverting apparatus 200 based on one or more sets of interconnecting tubular structures 202, 204 that, when implanted, redirect blood towards one or both of the kidney artery branches and act as obstructing component(s) within the vessel in order to cause an upstream buildup of blood pressure. For instance, the inlets 210, 212 of the tubular structures 202, 204 may be positioned within a patient's aorta and the outlets 220, 222 of the tubular structures 202, 204 may be positioned within the patient's right and left renal artery branches, respectively, such that a greater proportion of blood is directed to the right and left renal artery branches than without the implanted flow diverting apparatus 200.

Figure 3:
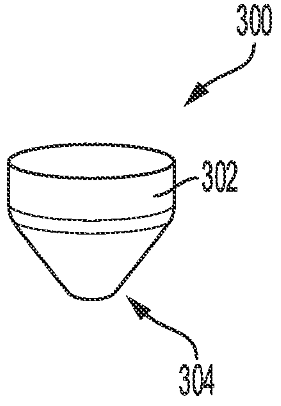
FIG. 3 illustrates a cone-shaped flow diverting apparatus, according to an aspect of the present disclosure.
Figure 4:
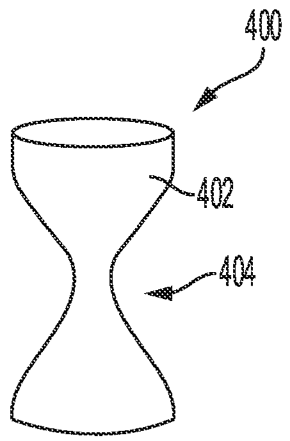
FIG. 4 illustrates an hour glass-shaped flow diverting apparatus, according to an aspect of the present disclosure.
Figure 5:
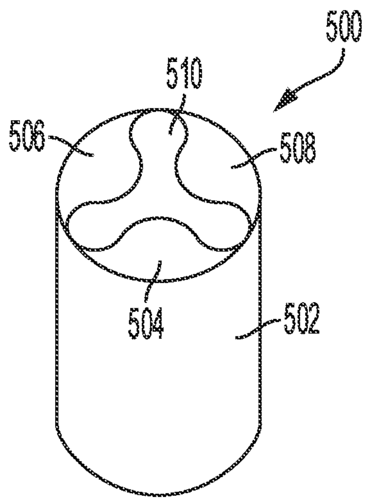
FIG. 5 illustrates a lobe-shaped flow diverting apparatus, according to an aspect of the present disclosure.

In other various examples, the flow diverting apparatus can have any suitable cone-shaped (e.g., FIG. 3), hourglass-shaped (e.g., FIG. 4) or lobe-shaped structure (e.g., FIG. 5) (which may have pockets that are liftable with fluid or gas) that is able to partially occlude flow through a vessel such as the infrarenal aorta or a vessel downstream the infrarenal aorta. FIG. 3 illustrates an example cone-shaped flow diverting apparatus 300 having a frame 302 that includes a narrowed portion 304 at its outlet. FIG. 4 illustrates an example hourglass-shaped flow diverting apparatus 400 that includes a frame 402 having a middle narrowed portion 404. FIG. 5 illustrates an example lobe-shaped flow diverting apparatus 500 that includes a frame 502 having multiple lobes 504, 506, 508 forming an interior 510. Blood may pass through the interior 510, but not through the lobes 504, 506, 508. In other examples, the flow diverting apparatus 500 may include any suitable quantity of lobes (e.g., 2, 4, 5, 10, etc.). In some aspects, only a middle portion of the flow diverting apparatus 500 includes the lobes 504, 506, 508. Stated differently, in such aspects, the flow diverting apparatus 500 may include an inlet and/or an outlet that does not includes lobes. In at least one example, the flow diverting apparatus may be the stent-graft disclosed in International Patent Application Publication WO2020/168216, one of the inventors of which is the inventor of the present patent application.

Figure 6:
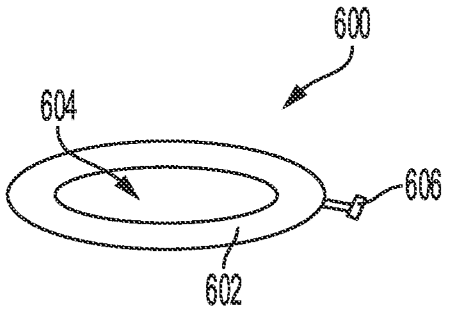
FIG. 6 illustrates a cuff-based flow diverting apparatus structure for extravascular implantation, according to an aspect of the present disclosure.

Examples of flow diverting apparatuses for an extravascular approach can be ring-shaped and/or band-shaped devices that may be balloon and/or cuff-based. In some aspects, such extravascular flow diverting apparatuses can include points along the apparatus that are responsible for anchorage and/or fastening to stabilize it in position and configuration. This can be achieved in order to constrict a vessel (e.g., the infrarenal aorta and/or a vessel(s) downstream the infrarenal aorta) from the exterior of the vessel (extravascularly). FIG. 6 illustrates an example cuff-based flow diverting apparatus 600 having a body 602 forming an interior 604. The body 602 may encircle a vessel from the exterior of the vessel such that the vessel is positioned within the interior 604. The flow diverting apparatus 600 may include a port 606 for inflating or deflating the body 602 through injection or aspiration of fluid or gas. The flow diverting apparatus 600 can be expanded or contracted to the desired extent in order to sufficiently narrow the vessel such that proximal pressure build-up necessary for hemodynamic stabilization to take place is achieved.

Figure 7:
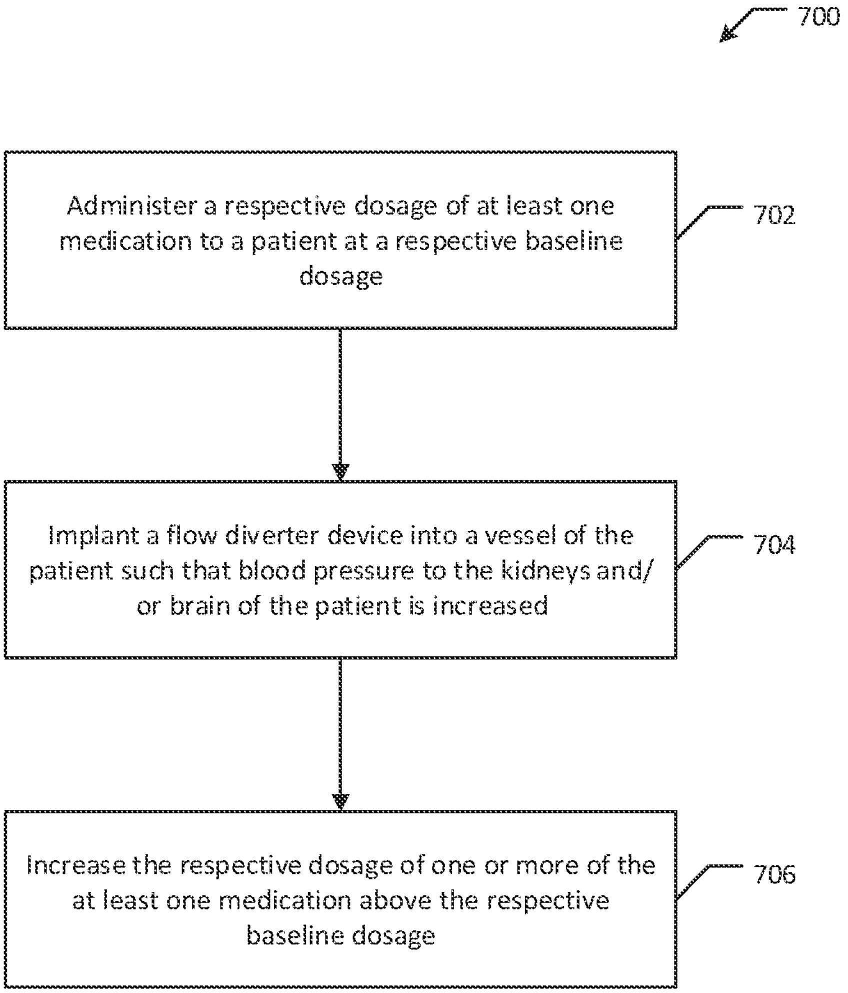
FIG. 7 illustrates a flow chart of an example method for administering at least one medication, according to an aspect of the present disclosure.

FIG. 7 shows a flow chart of an example method 700 for administering at least one medication. Although the example method 700 is described with reference to the flowchart illustrated in FIG. 7, it will be appreciated that many other methods of performing the acts associated with the method 700 may be used. For example, the order of some of the blocks may be changed, certain blocks may be combined with other blocks, and some of the blocks described are optional.

In various aspects, the method 700 may begin by administering at least one medication to a patient at a respective baseline dosage (block 702). The at least one medication is part of a therapeutic approach to treating the patient's cardiovascular disease. The at least one medication may be, for example, (i) air angiotensin-receptor blocker, (ii) an angiotensin receptor enzyme (ACE) inhibitor, (iii) a chymase inhibitor, (iv) an ACE inhibitor and an angiotensin-receptor blocker, (v) an angiotensin receptor blocker and a neprilysin-inhibitor, or (vi) a beta-blocker and an ACE inhibitor, an angiotensin-receptor blocker, or a neprilysin inhibitor. In various aspects, when more than one medication is administered to the patient, each medication is administered individually (e.g., not as a mixture). In one aspect, one or more medications may be administered as a mixture. For example, a neprilysin inhibitor saccubitril) may be mixed with an angiotensin receptor blocker (e.g., valsartan) in a single tablet. If more than one medication is administered to the patient, each medication is administered at its own respective baseline dosage. Examples of an angiotensin-receptor blocker include valsartan, losartan, candesartan, eprosartan, telmisartan, and irbesartan. Examples of an ACE inhibitor include enalapril, lisinopril, trandolapril, ramipril, captopril, quinapril, and cilazapril. Examples of a chymase inhibitor include SUNC8257, BAY 1142524, and Fulacimstat. An example of a neprilysin-inhibitor is saccubitril. Examples of a beta-blocker are bisoprolol, carvedilol, and metoprolol.

The baseline dosage at which the at least one medication is administered to the patient may be different based on the medication that is administered. The following example baseline dosages are illustrative and not intended to be limiting. One having skill in the relevant art will appreciate other suitable baseline dosages. If valsartan is administered, the baseline dosage of valsartan may be 20 mg, 40 mg, etc. per day. If losartan is administered, the baseline dosage of losartan may be 12.5 mg, 25 mg, etc. per day. If candesartan is administered, the baseline dosage of candesartan may be 4 mg, 8 mg, etc. per day. If eprosartan is administered, the baseline dosage of eprosartan may be 400 mg. 600 mg, etc. per day. If telmisartan is administered, the baseline dosage of telmisartan may be 20 mg, 40 mg, etc. per day. If irbesartan is administered, the baseline dosage of irbesartan may be 75 mg, 150 mg, etc. per day. If enalapril is administered, the baseline dosage of enalapril may be 2.5 mg, Sing, etc. per day. If lisinopril is administered, the baseline dosage of lisinopril may be 2.5 mg, 5 mg, etc. per day. If trandolapril is administered, the baseline dosage of trandolapril may be 1 mg, etc. per day. If ramipril is administered, the baseline dosage of ramipril may be 1.25 mg, 2.5 mg, etc. per day. If captopril is administered, the baseline dosage of captopril may be 18.75 mg, 37.5 mg, etc. per day. If quinapril is administered, the baseline dosage of quinapril may be 5 mg, 10 mg, etc. per day. If cilazapril is administered, the baseline dosage of cilazapril may be 0.5 mg, mg, etc. per day. If saccubitril is administered, the baseline dosage of saccubitril may be 24 mg, 49 mg, etc. per day. If bisoprolol is administered, the baseline dosage of bisoprolol may be 1.25 mg, 2.5 mg, etc. per day. If carvedilol is administered, the baseline dosage of carvedilol may be 3.125 mg, 6.25 mg, etc. per day. If metoprolol is administered, the baseline dosage of metoprolol may be 12.5 mg, 25 mg, etc. per day.

Figure 8:
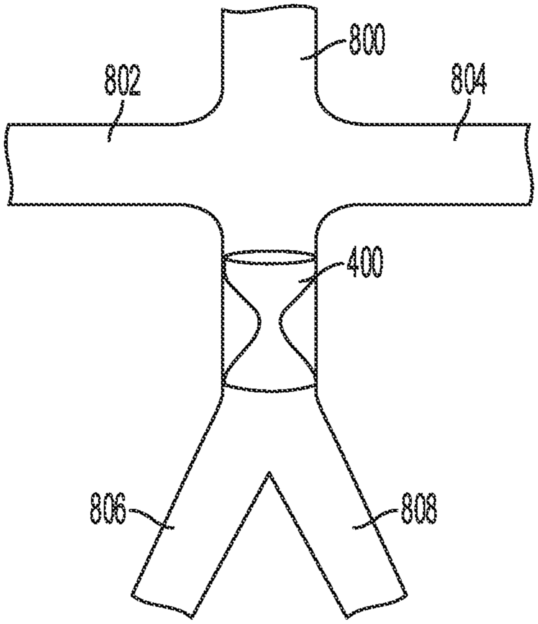
FIG. 8 illustrates a flow diverting apparatus implanted within an infrarenal aorta of a patient, according to an aspect of the present disclosure.

In at least some aspects, a flow diverting apparatus (e.g., the flow diverting apparatus 100, 200, 300, 400, 500, 600, or 700) may be implanted in the patient receiving the baseline dosage(s) of the at least one medication, relative a vessel of the patient, such that blood pressure to the patient's kidneys and/or brain is increased (block 704). For example, the flow diverting apparatus may be implanted intravascularly within the patient's vessel. In another example, the flow diverting apparatus may be implanted extravascularly on the exterior of the patient's vessel. In some aspects, the vessel is the patient's infrarenal aorta. FIG. 8 illustrates one example placement of the implanted flow diverting apparatus 400 within the patient's infrarenal aorta 800. While the flow diverting apparatus 400 is shown implanted intravascularly within the infrarenal aorta, in other examples, another suitable flow diverting apparatus may be implanted intravascularly or extravascularly at the same positioning relative to the infrarenal aorta 800. As shown in FIG. 8, the flow diverting apparatus 400 is implanted within the patient's infrarenal aorta 800 such that an inlet of the flow diverting apparatus 400 is downstream each of the renal artery branches 802 and 804 that lead to the patient's kidneys. Positioning the flow diverting apparatus 400 downstream the renal artery branches 802 and 804 helps create increased blood pressure to the renal artery branches 802 and 804, which can help reduce or eliminate the side effects that the patient experiences with an increased dosage of the at least one medication administered to the patient, as described above. Also shown in FIG. 8 for illustrative purposes is the right common iliac artery 806 and the left common iliac artery 808 of the patient.

Figure 9:
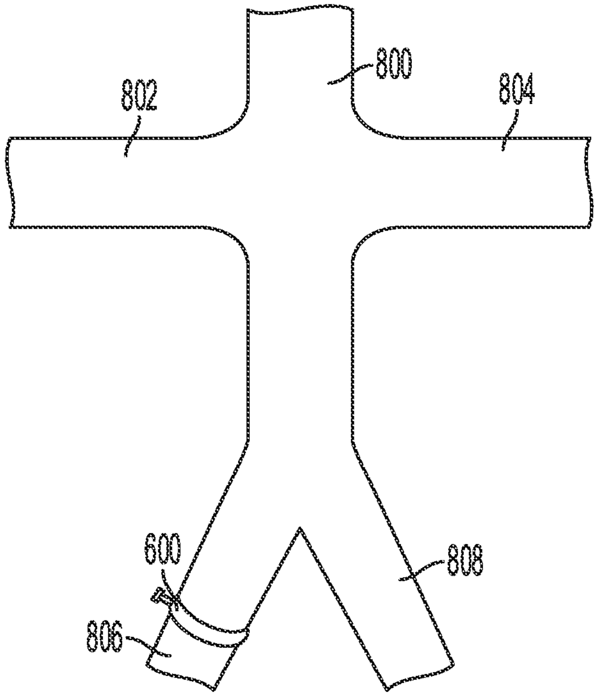
FIG. 9 illustrates a flow diverting apparatus implanted extravascularly with respect to the right common iliac artery of a patient, according to an aspect of the present disclosure.

In other aspects, the vessel may be a vessel of the patient that is downstream the patient's infrarenal aorta, such as the patient's right common iliac artery or superficial femoral artery and/or any other suitable blood vessel downstream the infrarenal aorta. Positioning the flow diverting apparatus downstream the patient's infrarenal aorta can still help create increased blood pressure to the kidney artery branches. FIG. 9 illustrates one example placement of the flow diverting apparatus 600 on the exterior of the patient's right common iliac artery 806. While the flow diverting apparatus 600 is shown implanted extravascularly on the right common iliac artery 806, in other examples, another suitable flow diverting apparatus may be implanted intravascularly or extravascularly at the same positioning relative to the right common iliac artery 806.

With the flow diverting apparatus implanted in the patient, the respective dosage of one or more of the at least one medication may be increased, or up-titrated, above the respective baseline dosage (block 706). For example, if an angiotensin receptor blocker is administered at a baseline dosage, then the angiotensin receptor blocker dosage may be increased. In another example, if an ACE inhibitor is administered at a baseline dosage, then the ACE inhibitor dosage may be increased. In another example still, if both an angiotensin-receptor blocker and an ACE inhibitor are each administered at respective baseline dosages, then the dosage of one or both of the angiotensin-receptor blocker and ACE inhibitor may be increased. In a further example, if both an angiotensin receptor blocker and a neprilysin-inhibitor are each administered at respective baseline dosages, then the dosage of one or both of the angiotensin receptor blocker and neprilysin-inhibitor may be increased. In a further example still, if a beta-blocker and another medication (e.g., an angiotensin receptor enzyme (ACE) inhibitor, an angiotensin-receptor blocker, or a neprilysin inhibitor) are each administered at respective baseline dosages, then the dosage of one or both of the beta-blocker and the other medication may be increased. In various aspects, the respective dosage may be increased shortly after implanting the flow diverting apparatus, such as one or two days after implanting the flow diverting apparatus.

In at least some aspects, the respective dosage of the one or more medications may be increased one or more times until the patient's hemodynamic status is stable. Whether a patient's hemodynamic status is stable is based on a variety of factors as one having skill in the relevant art will appreciate. A patient with a stable hemodynamic status does not have very low blood pressure (e.g., hypotension) or very high blood pressure (e.g., hypertension). A patient with a stable hemodynamic status has a normal resting heart rate (e.g., between 60 and 100 bpm). A patient with a stable hemodynamic status has at least a minimum perfusion threshold of blood to all parts of the patient's body (e.g., not having cold or ischemic tissue). A patient with a stable hemodynamic status does not have critically low oxygen saturation levels in any part of the patient's body. A patient with a stable hemodynamic status, after implantation of the flow diverter apparatus, does not have an undesirably elevated afterload pressure increase. A patient with a stable hemodynamic status does not have an undesirably elevated venous pressure nor fluid retention in areas of the body, such as the lower extremities.

The dosage amount to which the respective dosage of a medication may be increased can differ depending on the medication that is administered. The following example dosage amounts to which a medication may be increased are illustrative and not intended to be limiting. One having skill in the relevant art will appreciate other suitable dosage amounts. If valsartan is administered, in some examples, the valsartan dosage may be increased to an amount within a range of greater than or equal to 40 and less than or equal to 320 mg/day. For example, if valsartan is administered at a baseline dosage of 20 mg/day, then after implanting the flow diverting apparatus in the patient, the dosage of valsartan may be increased by an amount of 20 mg to a new dosage of 40 mg/day. If the patient's hemodynamic status is stable after increasing the valsartan dosage to 40 mg/day (e.g., after monitoring the patient for one or two weeks at the 40 mg/day dosage), then the valsartan dosage may be maintained at this increased dosage. If, on the other hand, the patient's hemodynamic status is not yet stable after increasing the valsartan dosage to 40 mg/day (e.g., after monitoring the patient for one or two weeks at the 40 mg/day dosage), then the valsartan dosage may be increased again, such as to 80 mg/day, and the patient's hemodynamic status may be monitored again (e.g., for one or two weeks). The process may be repeated until the patient's hemodynamic status is stable. The directly preceding example is illustrative of the way all the medications in the example method 700 may be increased following implantation of the flow diverting apparatus and therefore will not be repeated for each example medication.

In some examples, the valsartan dosage may be increased to an amount within a range of greater than or equal to 40 and less than 320 mg/day until the patient's hemodynamic status is stable. In some examples, this amount for valsartan can be 40 to 280 mg/day. In some examples, this amount for valsartan can be 40 to 240 mg/day. In some examples, this amount for valsartan can be 50 to 200 mg/day. In some examples, this amount for valsartan can be 75 to 150 mg/day. In some examples, this amount for valsartan can be 75 to 125 mg/day. In some examples, the administration of valsartan can be increased to 40, 80, 160, 240, 280, or 320 mg/day. In some examples, the administration of valsartan can be increased to an amount that is within a range of 101% to 800% of the baseline dosage of valsartan until the patient's hemodynamic status is stable. In some examples, this amount for valsartan can be 200% to 800% of the baseline dosage. In some examples, this amount for valsartan can be 200% to 600% of the baseline dosage. In some examples, this amount for valsartan can be 200% to 400% of the baseline dosage.

If losartan is administered, in some examples, the losartan dosage may be increased to an amount within a range of greater than or equal to 25 and less than or equal to 150 mg/day, in some examples, this range for losartan may be greater than or equal to 25 and less than or equal to 125 mg/day. In some examples, this range for losartan may be 25 to 100 mg/day. In some examples, this range for losartan m be 50 to 150 mg/day. In some examples, this range for losartan may be 50 to 100 mg/day. In some examples, the administration of losartan can be increased to a dosage of 25, 50, 75, or 100 mg/day. In some examples, the administration of losartan can be increased to an amount that is within a range of 101% to 400% of the baseline dosage of losartan. In some examples, this range for losartan may be 150% to 400% of the baseline dosage. In some examples, this range for losartan may be 200% to 400% of the baseline dosage. In some examples, this range for losartan may be 200% to 300% of the baseline dosage.

If candesartan is administered, in some examples, the candesartan dosage may be increased to an amount within a range of greater than or equal to 8 and less than or equal to 32 mg/day. In some examples, this range for candesartan may be greater than or equal to 8 and less than or equal to 24 mg/day. In some examples, the range for candesartan may be 16 to 32 mg/day. In some examples, the range for candesartan may be 8 to 16 mg/day. In some examples, the range for candesartan may be 10 to 20 mg/day. In some examples, the administration of candesartan can be increased to 4, 8, 16, 28, or 32 mg/day. In some examples, the administration of candesartan can be increased by an amount within a range of 101% to 800% of the baseline dosage of candesartan. In some examples, the range for candesartan may be 200% to 800% of the baseline dosage of candesartan. In some examples, the range for candesartan may be 300% to 800% of the baseline dosage of candesartan. In some examples, the range for candesartan may be 400% to 700% of the baseline dosage of candesartan.

If eprosartan is administered, in some examples, the eprosartan dosage may be increased to an amount within a range of greater than or equal to 500 and less than or equal to 800 mg/day. In some examples, this range for eprosartan may be greater than or equal to 600 and less or equal to 700 mg/day. In some examples, the range for eprosartan may be 500 to 700 mg/day. In some examples, the administration of eprosartan can be increased to 500, 600, or 800 mg/day. In some examples, the administration of eprosartan can be increased to an amount within a range of 101% to 200% of the baseline dosage of eprosartan. In some examples, the range for eprosartan may be 125% to 200% of the baseline dosage of eprosartan. In some examples, the range for eprosartan may be 150% to 200% of the baseline dosage of eprosartan.

If telmisartan is administered, in some examples, the telmisartan dosage may be increased to an amount within a range of greater than or equal to 40 and less than or equal to 80 mg/day. In some examples, this range for telmisartan may be greater than or equal to 40 and less or equal to 60 mg/day. In some examples, the range for telmisartan may be 60 to 80 mg/day. In some examples, the administration of telmisartan can be increased to 40, 60, or 80 mg/day. In some examples, the administration of telmisartan can be increased to an amount within a range of 101% to 400% of the baseline dosage of telmisartan. In some examples, the range for telmisartan may be 150% to 400% of the baseline dosage of telmisartan. In some examples, the range for telmisartan may be 200% to 400% of the baseline dosage of telmisartan. In some examples, the range for telmisartan may be 200% to 300% of the baseline dosage of telmisartan.

If irbesartan is administered, in some examples, the irbesartan dosage may be increased to an amount within a range of greater than or equal to 150 and less than or equal to 300 mg/day. In some examples, this range for irbesartan may be greater than or equal to 150 and less or equal to 250 mg/day. In some examples, the range for irbesartan may be 150 to 225 mg/day. In some examples, the range for irbesartan may be 200 to 300 mg/day. In some examples, the administration of irbesartan can be increased to 150, 200, 225, or 300 mg/day. In some examples, the administration of irbesartan can be increased to an amount within a range of 101% to 400% of the baseline dosage of irbesartan. In some examples, the range for irbesartan may be 150% to 400% of the baseline dosage of irbesartan. In some examples, the range for irbesartan may be 200% to 400% of the baseline dosage of irbesartan. In some examples, the range for irbesartan may be 250% to 400% of the baseline dosage of irbesartan. In some examples, the range for irbesartan may be 200% to 300% of the baseline dosage of irbesartan.

If enalapril is administered, in some examples, the enalapril dosage may be increased to an amount within a range of greater than or equal to 5 and less than or equal to 40 mg/day. In some examples, this range for enalapril may be greater than or equal to 5 and less or equal to 37.5 mg/day. In some examples, the range for enalapril may be 5 to 20 mg/day. In some examples, the range for enalapril may be 5 to 10 mg/day. In some examples, the administration of enalapril can be increased to 5, 10, 15, 17.5, or 20 mg/day. In some examples, the administration of enalapril can be increased to an amount within a range of 101% to 800% of the baseline dosage of enalapril per day. In some examples, the range for enalapril may be 200% to 800% of the baseline dosage of enalapril per day. In some examples, the range for enalapril may be 200% to 700% of the baseline dosage of enalapril per day. In some examples, the range for enalapril may be 200% to 600% of the baseline dosage of enalapril per day.

If lisinopril is administered, in some examples, the lisinopril dosage may be increased to an amount within a range of greater than or equal to 5 and less than or equal to 40 mg/day following implantation of a flow diverter apparatus. In some examples, this range for lisinopril may be greater than or equal to 5 and less or equal to 37.5 mg/day. In some examples, the range for lisinopril may be 5 to 20 mg/day. In some examples, the range for lisinopril may be 10 to 20 mg/day. In some examples, the administration of lisinopril can be increased to 5, 10, 15, 17.5, or 20 mg/day. In some examples, the administration of lisinopril can be increased to an amount within a range of 101% to 800% of the baseline dosage of lisinopril. In some examples, the range for lisinopril may be 200% to 800% of the baseline dosage of lisinopril. In some examples, the range for lisinopril may be 200% to 700% of the baseline dosage of lisinopril. In some examples, the range for lisinopril may be 200% to 600% of the baseline dosage of lisinopril.

If trandolapril is administered, in some examples, the trandolapril dosage may be increased to an amount within a range of greater than or equal to 2 and less than or equal to 4 mg/day. In some examples, this range for trandolapril may be greater than or equal to 2.5 and less or equal to 4 mg/day. In some examples, the range for trandolapril may be 2.5 to 3.5 mg/day. In some examples, the range for trandolapril may be 2 to 3 mg/day. In some examples, the administration of trandolapril can be increased to 2, 3, or 4 mg/day. In some examples, the administration of trandolapril can be increased to an amount within a range of 101% to 400% of the baseline dosage of trandolapril. In some examples, the range for trandolapril may be 150% to 400% of the baseline dosage of trandolapril. In some examples, the range for trandolapril may be 200% to 400% of the baseline dosage of trandolapril.

If ramipril is administered, in some examples, the ramipril dosage may be increased to an amount within a range of greater than or equal to 2.5 and less than or equal to 10 mg/day. In some examples, the range for ramipril may be 5 to 10 nag/day. In some examples, the range for ramipril may be 2.5 to 7.5 mg/day. In some examples, the administration of ramipril can be increased to 2.5, 3.75, 5, 7.5, 8.75, or 10 mg/day. In some examples, the administration of ramipril can be increased to an amount within a range of 101% to 800% of the baseline dosage of ramipril. In some examples, the range for ramipril nay be 150% to 800% of the baseline dosage of ramipril. In some examples, the range for ramipril may be 200% to 800% of the baseline dosage of ramipril, in some examples, the range for ramipril may be 300% to 800% of the baseline dosage of ramipril. In some examples, the range for ramipril may be 200% to 700% of the baseline dosage of ramipril. In some examples, the range for ramipril may be 200% to 600% of the baseline dosage of ramipril.

If captopril is administered, in some examples, the captopril dosage may be increased to an amount within a range of greater than or equal to 37.5 and less than or equal to 450 mg/day. In some examples, this range for captopril may be greater than or equal to 37.5 and less or equal to 300 mg/'day. In some examples, the range for captopril nay be 37.5 to 100 mg/day. In some examples, the range for captopril may be 75 to 125 mg/day. In some examples, the administration of captopril can be increased to 37.5, 56.25, 75, 87.5, 93.75, 112.5, 131.25, 150, 168.75, 187.5, 206.25, 225, 243.75, 262.5, 281.25, 300, 318.75, 337.5, 356, 374.75, 393.5, 412.25, 431, or 449.75 mg/day. In some examples, the administration of captopril can be increased to an amount within a range of 101% to 1200% of the baseline dosage of captopril. In some examples, the range for captopril may be 200% to 1200% of the baseline dosage of captopril. In some examples, the range for captopril may be 200% to 1000% of the baseline dosage of captopril. In some examples, the range for captopril may be 200% to 800% of the baseline dosage of captopril. In some examples, the range for captopril may be 300% to 1000% of the baseline dosage of captopril.

If quinapril is administered, in some examples, the quinapril dosage may be increased to an amount within a range of greater than or equal to 10 and less than or equal to 40 mg/day. In some examples, this range for quinapril may be greater than or equal to 10 and less or equal to 20 mg/day. In some examples, the range for quinapril may be 20 to 40 mg/day. In some examples, the range for quinapril may be 20 to 30 mg/day. In some examples, the administration of quinapril can be increased to 10, 15, 20, 30, or 40 mg/day. In some examples, the administration of quinapril can be increased to an amount within a range of 101% to 800% of the baseline dosage of quinapril. In some examples, the range for quinapril may be 200% to 800% of the baseline dosage of quinapril. In some examples, the range for quinapril may be 200% to 600% of the baseline dosage of quinapril.

If cilazapril is administered, in some examples, the cilazapril dosage may be increased to an amount within a range of greater than or equal to 1 and less than or equal to 5 mg/day. In some examples, this range for cilazapril may be greater than or equal to 1 and less or equal to 4.5 mg/day. In some examples, the range for cilazapril may be 1 to 4 mg/day. In some examples, the range for cilazapril may be 1 to 3 mg/day. In some examples, the administration of cilazapril can be increased to 1, 1.5, 2.5, 4, or 5 mg/day. In some examples, the administration of cilazapril can be increased to an amount within a range of 101% to 1000% of the baseline dosage of cilazapril. In some examples, the range for cilazapril may be 200% to 1000% of the baseline dosage of cilazapril. In some examples, the range for cilazapril may be 200% to 900% of the baseline dosage of cilazapril. In some examples, the range for cilazapril may be 200% to 800% of the baseline dosage of cilazapril.

If saccubitril is administered, in some examples, the saccubitril dosage may be increased to an amount within a range of greater than or equal to 97 and less than or equal to 194 mg/day. In some examples, this range for saccubitril may be greater than or equal to 97 and less or equal to 170 mg/day. In some examples, the range for saccubitril may be 97 to 145 mg/day. In some examples, the range for saccubitril may be 120 to 194 mg/day. In some examples, the administration of saccubitril can be increased to an amount within a range of 101% to 800% of the baseline dosage of saccubitril. In some examples, the range for saccubitril may be 200% to 800% of the baseline dosage of saccubitril. In some examples, the range for saccubitril may be 200% to 700% of the baseline dosage of saccubitril. In some examples, the range for saccubitril may be 200% to 600% of the baseline dosage of saccubitril.

If bisoprolol is administered, in some examples, the bisoprolol dosage may be increased to an amount within a range of greater than or equal to 2.5 mg and less than or equal to 20 mg/day. In some examples, this range for bisoprolol may be 2.5 to 10 mg/day. In some examples, the administration of bisoprolol can be increased to 2.5, 5, 10, or 20 mg/day. In some examples, the administration of bisoprolol can be increased to an amount within a range of 101% to 800% of the baseline dosage of bisoprolol. In some examples, the range for bisoprolol may be 200% to 800% of the baseline dosage of bisoprolol. In some examples, the range for bisoprolol may be 200% to 700% of the baseline dosage of bisoprolol. In some examples, the range for bisoprolol may be 200% to 600% of the baseline dosage of bisoprolol.

If carvedilol is administered, in some examples, the carvedilol dosage may be increased to an amount within a range of greater than or equal to 6.25 mg and less than or equal to 100 mg/day. In some examples, this range for carvedilol may be 6.25 to 50 mg/day. In some examples, the administration of carvedilol can be increased to 6.25, 12.5, 25, 50, or 100 mg/day. In some examples, the administration of carvedilol can be increased to an amount within a range of 101% to 3200% of the baseline dosage of carvedilol. In some examples, the range for carvedilol may be 200% to 3200% of the baseline dosage of carvedilol. In some examples, the range for carvedilol may be 200% to 1600% of the baseline dosage of carvedilol.

If metoprolol is administered, in some examples, the metoprolol dosage may be increased to an amount within a range of greater than or equal to 25 mg and less than or equal to 200 mg/day. In some examples, this range for metoprolol may be 25 to 150 mg/day. In some examples, the administration of metoprolol can be increased to 25, 50, 100, or 200 mg/day. In some examples, the administration of metoprolol can be increased to an amount within a range of 101% to 1600% of the baseline dosage of metoprolol. In some examples, the range for metoprolol may be 200% to 1600% of the baseline dosage of metoprolol. In some examples, the range for metoprolol may be 200% to 800% of the baseline dosage of metoprolol.

In some aspects, the example method 700 may include administering one or more medications to the patient subsequent to implanting the flow diverting apparatus that were not administered to the patient prior to implanting the flow diverting apparatus. For example, an angiotensin-receptor blocker may be administered to the patient at a baseline dosage prior to implanting the flow diverting apparatus. Then, at some point subsequent to implanting the flow diverting apparatus the patient may be started on an ACE inhibitor or a neprilysin-inhibitor alongside the use of the angiotensin-receptor blocker. The patient may be started on one of the baseline dosages previously described for the ACE inhibitor or the neprilysin-inhibitor. In another example, an ACE inhibitor may be administered to the patient at a baseline dosage prior to implanting the flow diverting apparatus. Then, at some point subsequent to implanting the flow diverting apparatus, the patient may be started on an angiotensin-receptor blocker. The patient may be started on one of the baseline dosages previously described for the angiotensin-receptor blocker.

Figure 10:
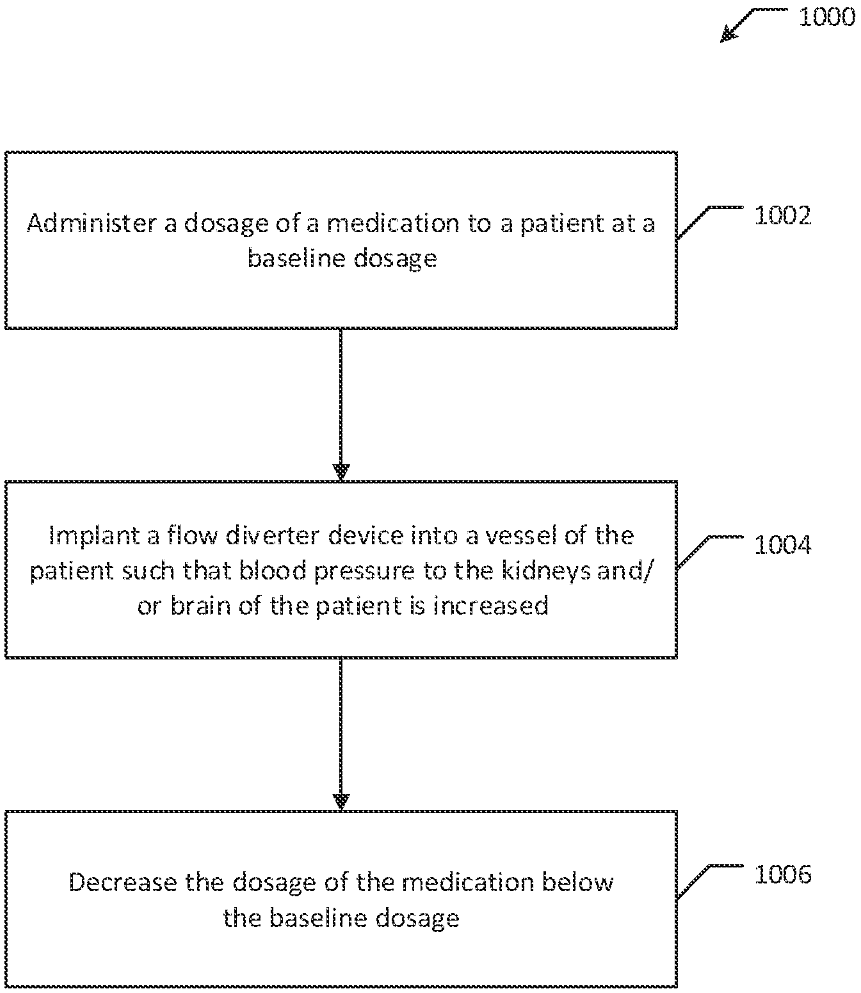
FIG. 10 illustrates a flow chart of an example method for administering a medication, according to an aspect of the present disclosure.

FIG. 10 shows a flow chart of an example method 1000 for administering a medication. Although the example method 1000 is described with reference to the flowchart illustrated in FIG. 10, it will be appreciated that many other methods of performing the acts associated with the method 1000 may be used. For example, the order of some of the blocks may be changed, certain blocks may be combined with other blocks, and some of the blocks described are optional.

In various aspects, the method 1000 may begin administering a medication (e.g., a diuretic) to a patient at a baseline dosage (block 1002). In at least some aspects, the diuretic is administered as part of a therapeutic approach to treating the patient's cardiovascular disease. Example diuretics include furosemide, torsemide, bumetanide, metolazone, chlorothiazide, hydrochlorothiazide, indapamide, chlorothalidone, spironolactone, and eplerenone. In some aspects, more than one diuretic may be administered to the patient. In some instances of such aspects, each diuretic may be administered individually (e.g., not as a mixture). In other instances, one or more diuretics may be administered as a mixture (e.g., from a single infusion bag within which the one or more diuretics are mixed). When more than one diuretic is administered, each diuretic is administered at its own respective baseline dosage.

The baseline dosage at which the diuretic is administered to the patient may be different based on the medication that is administered. The following example baseline dosages are illustrative and not intended to be limiting. One having skill in the relevant art will appreciate other suitable baseline dosages. If furosemide is administered, the baseline dosage of furosemide may be 200 mg, 400 mg. 620 mg, etc. per day. If torsemide is administered, the baseline dosage of torsemide may be 100 mg, 120 mg, 220 mg, etc. per day. If bumetanide is administered, the baseline dosage of bumetanide may be 8 mg, 9 mg, 10.5 mg, etc. per day. If metolazone is administered, the baseline dosage of metolazone may be 12.5 mg, 15 mg, 150 mg, 305 mg, etc. per day. If chlorothiazide is administered, the baseline dosage of chlorothiazide may be 1000 mg, 2000 mg, etc. per day. If hydrochlorothiazide is administered, the baseline dosage of hydrochlorothiazide may be 100 mg, 212.5 mg, etc. per day. If indapamide is administered, the baseline dosage of indapamide may be 2.5 mg, 5 mg, etc. per day. If chlorthalidone is administered, the baseline dosage of chlorthalidone may be 100 mg, 200 mg, etc. per day. If spironolactone is administered, the baseline dosage of spironolactone may be 25 mg. 50 mg, 225 mg, per day. If eplerenone is administered, the baseline dosage of eplerenone may be 50 mg, 100 mg etc. per day.

In at least some aspects, a flow diverting apparatus (e.g., the flow diverting apparatus 100, 200, 300, 400, 500, 600, or 700) may be implanted in the patient receiving the baseline dosage of the diuretic, relative a vessel of the patient, such that blood pressure to the patient's kidneys and/or brain is increased (block 1004). For example, the flow diverting apparatus may be implanted intravascularly within the patient's vessel, such as described above in connection with FIG. 8, In another example, the flow diverting apparatus may be implanted extravascularly on the exterior of the patient's vessel, such as described above in connection with FIG. 9. The flow diverting apparatus may be implanted in the patient's infrarenal aorta, such as described above in connection with FIG. 8, or in another suitable vessel downstream the patient's infrarenal aorta, such as described above in connection with FIG. 9.

With the flow diverting apparatus implanted in the patient, the dosage of the diuretic may be decreased, or down-titrated, below the baseline dosage (block 1006). In at least some aspects, the diuretic dosage may be decreased one or more times until the patient's hemodynamic status is stable. A patient with a stable hemodynamic status is described above. The dosage to which the diuretic dosage may be decreased (e.g., until the patient's hemodynamic status is stable) can differ depending on the medication that is administered. The following example dosages are illustrative and not intended to be limiting. One having skill in the relevant art will appreciate other suitable dosages.

If furosemide is administered, in some examples, the furosemide dosage may be decreased to an amount within a range of between 20 and 600 mg/day. In some examples, this range for furosemide may be 20 to 60 mg/day. In some examples, the administration of furosemide can be decreased to 20, 40, 60, 80 mg/day. In some examples, the administration of furosemide can be decreased to an amount within a range of 25% to 99% of the baseline dosage of furosemide. In some examples, the range for furosemide may be 50% to 75% of the baseline dosage of furosemide.

If torsemide is administered, in some examples, the torsemide dosage may be decreased to an amount within a range of between 5 and 200 mg/day. In some examples, this range for torsemide may be 20 to 100 mg/day. In some examples, this range for torsemide may be 10 to 200 mg/day. In some examples, this range for torsemide may be 5 to 100 mg/day. In some examples, the administration of torsemide can be decreased to 5, 10, 15, 20, 80, 90, 95, or 100 mg/day. In some examples, the administration of torsemide can be decreased to an amount within a range of 50% to 99% of the baseline dosage of torsemide.

If bumetanide is administered, in some examples, the bumetanide dosage may be decreased to an amount within a range of between 0.5 and 10 mg/day. In some examples, this range for bumetanide may be 0.5 to 10 mg/day. In some examples, this range for bumetanide may be 1 to 10 mg/day. In some examples, this range for bumetanide may be 0.5 to 1.5 mg/day. In some examples, this range for bumetanide may be 1 to 1.5 mg/day. In some examples, the administration of bumetanide can be decreased to 0.5, 1, 1.5, or 2 mg/day. In some examples, the administration of bumetanide can be decreased to an amount within a range of 50% to 99% of the baseline dosage of bumetanide. In some examples, the range for bumetanide may be 50% to 75% of the baseline dosage of bumetanide.

If metolazone is administered, in some examples, the metolazone dosage may be decreased to an amount within a range of between 2.5 and 20 mg/day. In some examples, this range for metolazone may be 5 to 20 mg/day. In some examples, this range for metolazone may be 2.5 to 10 mg/day. In some examples, the administration of metolazone can be decreased to 2.5, 5, 7.5, or 10 mg/day. In some examples, the administration of metolazone can be decreased to an amount within a range of 50% to 99% of the baseline dosage of metolazone. In some examples, the range for metolazone may be 50% to 75% of the baseline dosage of metolazone.

If chlorothiazide is administered, in some examples, the chlorothiazide dosage may be decreased to an amount within a range of between 50 and 1000 mg/day. In some examples, this range for chlorothiazide may be 50 to 200 mg/day. In some examples, this range for chlorothiazide may be 250 to 1000 mg/day. In some examples, the administration of chlorothiazide can be decreased by 250 or 500 mg/day. In some examples, the administration of chlorothiazide can be decreased to an amount within a range of 50% to 99% of the baseline dosage of chlorothiazide. In some examples, the range for chlorothiazide may be 50% to 75% of the baseline dosage of chlorothiazide.

If hydrochlorothiazide is administered, in some examples, the hydrochlorothiazide dosage may be decreased to an amount within a range of between 12.5 and 200 mg/day. In some examples, this range for hydrochlorothiazide may be 25 to 200 mg/day. In some examples, this range for hydrochlorothiazide may be 12.5 to 150 mg/day. In some examples, this range for hydrochlorothiazide may be 25 to 150 mg/day. In some examples, the administration of hydrochlorothiazide can be decreased to 12.5, 25, 37.5, or 50 mg/day. In some examples, the administration of hydrochlorothiazide can be decreased to an amount within a range of 50% to 99% of the baseline dosage of hydrochlorothiazide. In some examples, the range for hydrochlorothiazide may be 50% to 75% of the baseline dosage of hydrochlorothiazide.

If indapamide is administered, in some examples, the indapamide dosage may be decreased to an amount within a range of between 1.25 and 3.75 mg/day. In some examples, this range for indapamide may be 1.25 to 2.5 mg/day. In some examples, the administration of indapamide can be decreased by 2.5 to 3.5 mg/day. In some examples, the administration of indapamide can be decreased to an amount within a range of 33% to 99% of the baseline dosage of indapamide. In some examples, the range for indapamide may be 50% to 99% of the baseline dosage of indapamide.

If chlorothalidone is administered, in some examples, the chlorothalidone dosage may be decreased to an amount within a range of between 15 and 150 mg/day. In some examples, this range for chlorothalidone may be 75 to 125 mg/day. In some examples, the administration of chlorothalidone can be decreased to 15, 25, 50, 75, or 100 mg/day. In some examples, the administration of chlorthalidone can be decreased to an amount within a range of 25% to 99% of the baseline dosage of chlorothalidone. In some examples, the range for chlorthalidone may be 50% to 75% of the baseline dosage of chlorthalidone.

If spironolactone is administered, in some examples, the spironolactone dosage may be decreased to an amount within a range of between 25 and 200 mg/day. In some examples, this range for spironolactone may be 25 to 100 mg/day. In some examples, the administration of spironolactone can be decreased to 25, 50, 75, or 100 mg/day. In some examples, the administration of spironolactone can be decreased to an amount within a range of 50% to 99% of the baseline dosage of spironolactone. In some examples, the range for spironolactone may be 50% to 75% of the baseline dosage of spironolactone.

If eplerenone is administered, in some examples, the eplerenone dosage may be decreased to an amount within a range of between 25 and 50 mg/day. In some examples, the administration of eplerenone can be decreased by 25 or 50 mg/day. In some examples, the administration of eplerenone can be decreased to an amount within a range of 50% to 99% of the baseline dosage of eplerenone. In some examples, the range for eplerenone may be 50% to 75% of the baseline dosage of eplerenone.

For any of the above example rates of decrease for the example diuretics, in some aspects, a medication may be decreased once per day over a series of consecutive days (e.g., until the patient's hemodynamic status is stable). In other aspects, the example method 1100 may include periods of maintaining a constant dosage of the medication between periods of decrease. For example, on a first day, a diuretic dosage may be decreased, on a second day that dosage may be maintained, and on a third day the diuretic dosage may be decreased again. In another example, on a first day, a diuretic dosage may be decreased, and two weeks later the diuretic dosage may be decreased again.

In various instances of cardiovascular disease treatment, a patient may be administered both a diuretic and one or more of a beta-blocker, an ACE inhibitor, an angiotensin-receptor blocker, a chymase inhibitor, and a neprilysin inhibitor. In such instances, a dosage of the administered diuretic may be decreased on the same day that a dosage of the administered beta-blocker. ACE inhibitor, angiotensin-receptor blocker, chymase inhibitor, and/or neprilysin inhibitor is increased. Stated differently, in some aspects, the example methods 700 and 1100 may be combined such that the example method 700 includes decreasing a dosage of a diuretic below a baseline dosage of that diuretic administered to the patient or the example method 1100 includes increasing a dosage of one or more of a beta-blocker, ACE inhibitor, angiotensin-receptor blocker, chymase inhibitor, and neprilysin inhibitor above a baseline dosage administered to the patient.

All numerical ranges herein should be understood to include all integers, whole or fractions, within the range and are inclusive of the ends of the range unless stated otherwise. For example, a range of 50 to 100 includes 50 and 100 within the range, whereas a range of greater than 0 and less than or equal to 50 does not include 0 in the range, but does include 50 in the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A method for administering at least one medication comprising:

administering a respective dosage of each of the at least one medication to a patient at a respective baseline dosage;

implanting a flow diverting apparatus in the patient receiving the respective baseline dosage of each of the at least one medication, the flow diverting apparatus being implanted at least one of intravascularly within an interior of a vessel of the patient and extravascularly on an exterior of the vessel of the patient, such that blood pressure to the kidneys and/or brain of the patient is increased, wherein the flow diverting apparatus is configured to partially occlude blood flow through the vessel when implanted to thereby increase blood pressure upstream of the implanted flow diverting apparatus; and increasing the respective dosage of one or more of the at least one medication above the respective baseline dosage subsequent to implanting the flow diverting apparatus, wherein the at least one medication is: (i) an angiotensin-receptor blocker, (ii) an angiotensin converting enzyme (ACE) inhibitor, (iii) a chymase inhibitor, (iv) an ACE-inhibitor and an angiotensin-receptor blocker, (v) an angiotensin receptor blocker and a neprilysin-inhibitor, or (vi) a beta-blocker and an ACE-inhibitor, an angiotensin-receptor blocker, or a neprilysin inhibitor.

2. The method of claim 1, wherein the flow diverting apparatus includes an inflatable member, a stent, or a stent-graft.

3. The method of claim 1, wherein the vessel is the infrarenal aorta or a vessel downstream the infrarenal aorta.

4. The method of claim 1, wherein prior to implanting the flow diverting apparatus into the patient, a respective dosage of the at least one medication above the respective baseline dosage causes the patient to experience negative side effects of the at least one medication.

5. The method of claim 1, wherein the increasing the respective dosage of one or more of the at least one medication above the respective baseline dosage subsequent to implanting the flow diverting apparatus comprises increasing the respective dosage of the one or more of the at least one medication one or more times until a hemodynamic status of the patient is stable.

6. The method of claim 1, wherein the at least one medication is a first medication, the method further comprising administering a dosage of a second medication to the patient subsequent to implanting the flow diverting apparatus.

7. The method of claim 6, wherein the second medication is an ACE-inhibitor, an angiotensin receptor blocker, or a neprilysin-inhibitor.

8. The method of claim 1, further comprising increasing the respective increased dosage of the one or more of the at least one medication after a period of maintaining the respective increased dosage.

9. The method of claim 8, wherein the period is greater than or equal to one week and less than or equal to two weeks.

10. The method of claim 1, wherein the at least one medication is one of the angiotensin-receptor blockers in the group consisting of valsartan, losartan, candesartan, eprosartan, telmisartan, and irbesartan.

11. The method of claim 10, wherein if the at least one medication is valsartan, the increasing the respective dosage of one or more of the at least one medication above the respective baseline dosage subsequent to implanting the flow diverting apparatus comprises increasing the respective dosage of valsartan to a dosage within a range of greater than or equal to 40 and less than or equal to 320 mg/day;

if the at least one medication is losartan, the increasing the respective dosage of one or more of the at least one medication above the respective baseline dosage subsequent to implanting the flow diverting apparatus comprises increasing the respective dosage of losartan to a dosage within a range of greater than or equal to 25 and less than or equal to 150 mg/day;

if the at least one medication is candesartan, the increasing the respective dosage of one or more of the at least one medication above the respective baseline dosage subsequent to implanting the flow diverting apparatus comprises increasing the respective dosage of candesartan to a dosage within a range of greater than or equal to 8 and less than or equal to 32 mg/day;

if the at least one medication is eprosartan, the increasing the respective dosage of one or more of the at least one medication above the respective baseline dosage subsequent to implanting the flow diverting apparatus comprises increasing the respective dosage of eprosartan to a dosage is within a range of greater than or equal to 500 and less than or equal to 800 mg/day;

if the at least one medication is telmisartan, the increasing the respective dosage of one or more of the at least one medication above the respective baseline dosage subsequent to implanting the flow diverting apparatus comprises increasing the respective dosage of telmisartan to a dosage within a range of greater than or equal to 40 and less than or equal to 80 mg/day; and if the at least one medication is irbesartan, the increasing the respective dosage of one or more of the at least one medication above the respective baseline dosage subsequent to implanting the flow diverting apparatus comprises increasing the respective dosage of irbesartan to a dosage within a range of greater than or equal to 150 and less than or equal to 300 mg/day.

12. The method of claim 1, wherein the at least one medication is one of the ACE-inhibitors in the group consisting of enalapril, lisinopril, trandolapril, ramipril, captopril, quinapril, and cilazapril.

13. The method of claim 12, wherein if the at least one medication is enalapril, the increasing the respective dosage of one or more of the at least one medication above the respective baseline dosage subsequent to implanting the flow diverting apparatus comprises increasing the respective dosage of enalapril to a dosage within a range of greater than or equal to 5 and less than or equal to 40 mg/day;

if the at least one medication is lisinopril, the increasing the respective dosage of one or more of the at least one medication above the respective baseline dosage subsequent to implanting the flow diverting apparatus comprises increasing the respective dosage of lisinopril to a dosage within a range of greater than or equal to 5 and less than or equal to 40 mg/day;

if the at least one medication is trandolapril, the increasing the respective dosage of one or more of the at least one medication above the respective baseline dosage subsequent to implanting the flow diverting apparatus comprises increasing the respective dosage of trandolapril to a dosage within a range of greater than or equal to 2 and less than or equal to 4 mg/day;

if the at least one medication is ramipril, the increasing the respective dosage of one or more of the at least one medication above the respective baseline dosage subsequent to implanting the flow diverting apparatus comprises increasing the respective dosage of ramipril to a dosage within a range of greater than or equal to 2.5 and less than or equal to 10 mg/day;

if the at least one medication is captopril, the increasing the respective dosage of one or more of the at least one medication above the respective baseline dosage subsequent to implanting the flow diverting apparatus comprises increasing the respective dosage of captopril to a dosage within a range of greater than or equal to 37.5 and less than or equal to 450 mg/day;

if the at least one medication is quinapril, the increasing the respective dosage of one or more of the at least one medication above the respective baseline dosage subsequent to implanting the flow diverting apparatus comprises increasing the respective dosage of quinapril to a dosage within a range of greater than or equal to 10 and less than or equal to 40 mg/day; and if the at least one medication is cilazapril, the increasing the respective dosage of one or more of the at least one medication above the respective baseline dosage subsequent to implanting the flow diverting apparatus comprises increasing the respective dosage of cilazapril to a dosage within a range of greater than or equal to 1 and less than or equal to 5 mg/day.

14. The method of claim 1, wherein the at least one medication is an angiotensin receptor blocker and a neprilysin-inhibitor, and wherein the neprilysin-inhibitor is sacubitril.

15. The method of claim 1, wherein the at least one medication is (1) a beta-blocker and (2) an ACE-inhibitor, an angiotensin-receptor blocker, or a neprilysin inhibitor, and wherein the beta-blocker is one of the medications in the group consisting of bisoprolol, carvedilol, and metoprolol.

16. The method of claim 15, wherein if the beta-blocker is bisoprolol, the increasing the respective dosage of one or more of the at least one medication above the respective baseline dosage subsequent to implanting the flow diverting apparatus comprises increasing the respective dosage of bisoprolol to a dosage within a range of greater than or equal to 2.5 and less than or equal to 20 mg per day until the patient's hemodynamic status is stable;

if the beta-blocker is carvedilol, the increasing the respective dosage of one or more of the at least one medication above the respective baseline dosage subsequent to implanting the flow diverting apparatus comprises increasing the respective dosage of carvedilol to a dosage within a range of greater than or equal to 6.25 and less than or equal to 100 mg per day until the patient's hemodynamic status is stable; and if the beta-blocker is metoprolol, the increasing the respective dosage of one or more of the at least one medication above the respective baseline dosage subsequent to implanting the flow diverting apparatus comprises increasing the respective dosage of metoprolol to a dosage within a range of greater than or equal to 25 and less than or equal to 200 mg per day until the patient's hemodynamic status is stable.

* * * * *